United States Patent
Sharma et al.

(10) Patent No.: US 8,945,519 B2
(45) Date of Patent: Feb. 3, 2015

(54) COMPOSITIONS USEFUL FOR TOOTH WHITENING

(71) Applicant: McNeil-PPC, Inc., Skillman, NJ (US)

(72) Inventors: Deepak Sharma, Flemington, NJ (US); Saroja Narasimhan, Matawa, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 13/759,422

(22) Filed: Feb. 5, 2013

(65) Prior Publication Data

US 2013/0149262 A1    Jun. 13, 2013

Related U.S. Application Data

(62) Division of application No. 11/859,953, filed on Sep. 24, 2007, now abandoned.

(51) Int. Cl.
| | |
|---|---|
| *A61K 8/22* | (2006.01) |
| *A61Q 11/00* | (2006.01) |
| *A61K 8/02* | (2006.01) |
| *A61K 8/06* | (2006.01) |
| *A61K 8/34* | (2006.01) |
| *A61K 8/60* | (2006.01) |
| *A61K 8/92* | (2006.01) |

(52) U.S. Cl.
CPC ............... *A61K 8/22* (2013.01); *A61K 8/0295* (2013.01); *A61K 8/068* (2013.01); *A61K 8/345* (2013.01); *A61K 8/60* (2013.01); *A61K 8/92* (2013.01); *A61Q 11/00* (2013.01)
USPC ............................................. 424/53; 424/49

(58) Field of Classification Search
CPC .................................. A61K 8/22; A61K 8/11
USPC ........................................................ 424/52, 53
See application file for complete search history.

(56) References Cited

U.S. PATENT DOCUMENTS

| | | | |
|---|---|---|---|
| 4,318,742 A | 3/1982 | Lokken | |
| 4,431,631 A * | 2/1984 | Clipper et al. | 424/53 |
| 4,971,782 A * | 11/1990 | Rudy et al. | 424/53 |
| 5,057,497 A | 10/1991 | Calam et al. | |
| 5,192,530 A * | 3/1993 | Gaffar et al. | 424/52 |
| 5,336,432 A | 8/1994 | Petchul et al. | |
| 6,365,134 B1 | 4/2002 | Orlowski et al. | |
| 6,669,930 B1 | 12/2003 | Hoic et al. | |
| 6,759,030 B2 | 7/2004 | Kosti | |
| 2003/0059450 A1 | 3/2003 | Maibach et al. | |
| 2005/0137109 A1 | 6/2005 | Quan et al. | |
| 2005/0176844 A1 | 8/2005 | Aasen et al. | |
| 2006/0024248 A1 | 2/2006 | Spengler et al. | |
| 2006/0178284 A1 | 8/2006 | Schmiedel et al. | |
| 2007/0166244 A1 * | 7/2007 | Ghosh et al. | 424/49 |

FOREIGN PATENT DOCUMENTS

| | | |
|---|---|---|
| DE | 202004013351 U1 | 10/2004 |
| KR | 2003037827 A | 5/2003 |
| RU | 2281083 C2 | 8/2006 |
| WO | WO 01/45649 A | 6/2001 |
| WO | WO 02/11688 A1 | 2/2002 |
| WO | WO 2006/098602 A | 9/2006 |

OTHER PUBLICATIONS

Burke, "Solubility Parameters: Theory and Application". The Book and Paper Group Annual 1984, vol. 3.
Mokhlis et al., "A Clinical Evaluation of Carbamide Peroxide and Hydrogen Peroxide Whitening Agents During Daytime Use." JADA 2000:131;1269-1277.
Vaughan, "Using Solubility Parameters in Cosmetic Formulation", *J. Soc. Cosmetics*, vol. 36 (Sep./Oct. 1985) pp. 319-333.
Vaughan, "Solubility Effects in Product, Package, Penetration, and Preservation", *Cosmetics & Toiletries*, vol. 103 (Oct. 1988) pp. 47-69.

* cited by examiner

*Primary Examiner* — Walter Webb

(57) ABSTRACT

The present invention provides tooth whitening compositions in the form of a liquid crystal or a microemulsion that includes a tooth whitening agent in an amount effective to whiten teeth, a hydrophilic phase including water, a hydrophobic phase including at least one oil, at least one anionic, nonionic, amphoteric or zwitterionic surfactant, and a water soluble co-solvent having a Hildebrand solubility parameter above 12 $(cal/cm^3)^{1/2}$, as well as methods for whitening teeth including applying the liquid crystal or microemulsion composition to the teeth for a period of time and under conditions effective to whiten the teeth.

8 Claims, No Drawings

COMPOSITIONS USEFUL FOR TOOTH WHITENING

This application is a divisional of U.S. application Ser. No. 11/859,953 filed Sep. 24, 2007, the complete disclosure of which is hereby incorporated herein by reference for all purposes.

FIELD OF THE INVENTION

The present invention relates to physically and chemically stable tooth whitening compositions in the form of liquid crystal gels or microemulsion liquids.

BACKGROUND OF THE INVENTION

In the dental industry, gels and pastes are utilized as vehicles for applying a variety of dentifrices, bleaching aids, remineralizing agents, and fluoride compounds to teeth. A gel is a colloid produced by combining a dispersed phase with a continuous phase (i.e. a dispersion medium or matrix) to produce a viscous, jelly-like, semisolid material. A "dental bleaching gel" is a gel that carries a bleaching agent that can be safely applied to teeth. Hydrogen peroxide and other peroxide producing sources have become the bleaching agents of choice for use in dental bleaching gels. Hydrogen peroxide is a powerful oxidizer, which serves to bleach the extrinsic and intrinsic chromogens in the teeth, thereby, producing a whiter appearance.

Viscosity is a very important parameter to control for effective dental bleaching gels, as it is a key determinant of peroxide release and in turn the whitening performance. Hydrogen peroxide is known to attack certain gelling agents and/or thickeners commonly used to make commercially available dental bleaching gels or pastes. For example, carboxypolymethylene thickeners conventionally used in whitening gels are susceptible to degradation by hydrogen peroxide under certain conditions. As a result of this attack, the gelling agents or thickeners break down over time; in some cases to such an extent that the gel's viscosity becomes too low to be suitable for use. Low viscosity gels flow uncontrollably from the dispensing tube, syringes etc. and become difficult to manipulate for their intended function. More importantly, if the viscosity is too low, the gel is more likely to flow away from the teeth, thus resulting in a reduced residence time and increased irritation due to undesired interaction of peroxide with soft tissues. Residence time is the time the dental bleaching gel actually is in contact with the tooth enamel.

Another problem associated with commercially available dental bleaching gels or pastes is that hydrogen peroxide tends to decompose at room temperature. The rate of this decomposition is dependent upon many factors. The presence of various metallic impurities, such as iron, manganese, copper and chromium, can catalyze the decomposition even when present in trace quantities. Furthermore, the stability of hydrogen peroxide decreases with increasing alkalinity and temperature, particularly in the presence of conventional thickeners such as carboxypolymethylene thickeners, in which case pH must be controlled by the use of pH buffers and the like. Because the whitening ability of a dental bleaching gel depends on the hydrogen peroxide concentration, premature decomposition diminishes the ability of the gel to whiten. Due to this instability, it has also been difficult to deliver other agents that can reduce sensitivity and increase remineralization.

One solution to these problems has been to refrigerate the dental bleaching gels or pastes until use. Refrigeration slows down the hydrogen peroxide attack on the gelling agent and also slows down hydrogen peroxide decomposition. However, refrigeration is both expensive and inconvenient. Various stabilizing agents have been investigated in an attempt to develop hydrogen peroxide containing dental bleaching gels and pastes that are stable at room temperature.

In view of the teachings of the prior art using conventional thickeners, there is a need for thermodynamically and chemically stable tooth whitening formulations that not only provide improved whitening but also provide a positive consumer experience.

SUMMARY OF THE INVENTION

The present invention provides tooth whitening compositions selected from the group consisting of a liquid crystal and a microemulsion composition and that includes a tooth whitening agent in an amount effective to whiten teeth, a hydrophilic phase including water, a hydrophobic phase including at least one oil, a surfactant selected from the group consisting anionic, nonionic, amphoteric and zwitterionic surfactants, and a water soluble co-solvent having a Hildebrand solubility parameter above 12 $(cal/cm^3)^{1/2}$, as well as methods for whitening teeth including applying a composition of the present invention to the teeth for a period of time and under conditions effective to whiten the teeth.

DETAILED DESCRIPTION OF THE INVENTION

As used herein, the term microemulsion refers to clear, isotropic liquid mixtures of oil, water and surfactant. The microemulsions ("MEs") may be oil-in-water ("O/W"), where oil is the dispersed phase and water is the continuous phase, or water-in-oil ("W/O"), where water is the dispersed phase and oil is the continuous phase. The compositions are substantially transparent or translucent and particles of the dispersed phase have a particle size of less than about 150 nanometers.

Liquid crystals are substances that exhibit properties between those of a conventional liquid and those of a solid crystal. For instance, a liquid crystal ("LC") may flow like a liquid or gel, but have the molecules in the liquid arranged and oriented in a crystal-like way. LCs contain oil, water, surfactant and co-surfactant. Both LCs and MEs can solubilize active ingredients in their micelles or surfactant bilayers and aid in targeted delivery to the desired substrate. Formulating these systems with a solubilized oil phase in the formula may change the partition coefficient of hydrogen peroxide. In addition, due to the small particle size of the dispersed phase in compositions of the present invention, there is more uniformity in the deposition of actives onto teeth.

The compositions of the present invention include a whitening agent in an amount effective to whiten the teeth. The whitening agent may be selected from a peroxide compound, e.g. hydrogen peroxide, or any compound that yields hydrogen peroxide when placed in an aqueous medium. For example, carbamide peroxide generates hydrogen peroxide when placed in water. Other names for carbamide peroxide include urea peroxide, urea hydrogen peroxide, hydrogen peroxide carbamide and perhydrol urea. Hydrogen peroxide conjugated to hydrophilic glass transition polymers, e.g. peroxydone, PVP-K90, PVP-K30, PVP-XL10, can also be used as a source of hydrogen peroxide. The amount of whitening agent utilized in the compositions of the present invention may range from about 0.1% to about 50%, for example about 1% to about 35%, by weight of the composition. Higher amounts of whitening agent are preferred so that the composition may serve as a "fast acting whitening gel", capable of whitening teeth with only one or two applications.

The compositions of the present invention contain a hydrophilic phase that typically comprises water. The amount of water in the composition will vary, depending on whether the composition is O/W or W/O, and whether the composition is a LC or a ME. For LCs, the amount of water may range from about 1 to about 60% by weight of the composition. For MEs, the amount of water may range from about 1 to about 80% by weight of the composition.

The compositions of the present invention also contain a hydrophobic phase that typically comprises, or consists essentially of, an oil. The oil typically has a Hildebrand solubility parameter value ranging from about 5 to 15, or from about 5 to about 12 $(cal/cm^3)^{1/2}$. Suitable oils include, but are not limited to, coconut oil, clove oil, mineral oil, isopropyl myristate, linseed oil, octyl palmitate, and the like, as well as those listed in the cited Journal articles. The Hildebrand solubility parameters are generally available by referring to standard chemistry textbooks or similar reference manuals. The Journal of the Society of Cosmetic Chemistry, Volume 36, pages 319-333, and Cosmetics and Toiletries, Vol. 103, October 1988, pages 47-69, list the Hildebrand solubility parameter values for a wide variety of cosmetic ingredients and how the solubility parameter is calculated. For LCs, the amount of oil may range from about 1% to less than 50%, or from about 1% to about 30%, or from about 1% to about 25%, by weight of the composition. For MEs, the amount of oil may range from about 1% to less than 50%, or from about 1% to about 25%, or from about 1 to about 10%, by weight of the composition. For the compositions of the present invention, the hydrophilic phase is in predominant weight proportion relative to the hydrophobic phase. Typically, the weight ratio of hydrophilic phase to hydrophobic phase in compositions of the present invention may range from about 1.5:1 to about 10:1, or from about 2:1 to about 5:1.

The compositions of the present invention contain at least one surfactant. As used herein, a surfactant is an organic, amphiphilic, surface-active ingredient capable of interacting with the water phase and the oil phase to form lyotropic liquid crystals and/or O/W or W/O microemulsions. Suitable surfactants include, but are not limited to, anionic, nonionic, amphoteric or zwitterionic surfactants.

Suitable anionic surfactants include alkyl sulfates and alkyl ether sulfates and their salts having a water-soluble cation, such as ammonium, sodium, potassium or triethanolamine. Another type of anionic surfactant that may be used in the compositions of the invention are water-soluble salts of organic, sulfuric acid reaction products. Examples of such anionic surfactants are salts of organic sulfuric acid reaction products of hydrocarbons, such as n-paraffins having 8 to 24 carbon atoms, and a sulfonating agent, such as sulfur trioxide. Also suitable as anionic surfactants are reaction products of fatty acids esterified with isethionic acid and neutralized with sodium hydroxide. The fatty acids may be derived from coconut oil, for example. In addition, succinates and succinimates are suitable anionic surfactants. This class includes compounds such as disodium N-octadecylsulfosuccinate; tetrasodium N-(1,2-dicarboxyethyl)-N-octadecylsulfosuccinate; and esters of sodium sulfosuccinic acid, e.g. the dihexyl ester of sodium sulfosuccinic acid, the dioctyl ester of sodium sulfosuccinic acid, and the like. Other suitable anionic surfactants include olefin sulfonates having about 12 to 24 carbon atoms. The term "olefin sulfonate" means a compound that can be produced by sulfonation of an alpha olefin by means of uncomplexed sulfur trioxide, followed by neutralization of the acid reaction mixture in conditions such that any sultones that have been formed in the reaction are hydrolyzed to give the corresponding hydroxy-alkanesulfonates. The alpha-olefin from which the olefin sulfonate is derived is a mono-olefin having about 12 to 24 carbon atoms, preferably about 14 to 16 carbon atoms. Other classes of suitable anionic organic surfactants are the beta-alkoxy alkane sulfonates or water-soluble soaps thereof such as the salts of C-substituted 10-20 fatty acids, for example coconut and tallow based soaps. Preferred salts are ammonium, potassium, and sodium salts. Still another class of anionic surfactants includes N-acyl amino acid surfactants and salts thereof (alkali, alkaline earth, and ammonium salts). Examples of such surfactants are the N-acyl sarcosinates, including lauroyl sarcosinate, myristoyl sarcosinate, cocoyl sarcosinate, and oleoyl sarcosinate, preferably in sodium or potassium forms.

The composition may contain one or more nonionic surfactants in lieu of, or in addition to, the anionic surfactant. Nonionic surfactants are generally compounds produced by the condensation of alkylene oxide groups with a hydrophobic compound. Suitable classes of nonionic surfactants include: (a) long chain dialkyl sulfoxides containing one short chain alkyl or hydroxy alkyl radical of from about 1 to 3 carbon atoms and one long hydrophobic chain which may be an alkyl, alkenyl, hydroxyalkyl, or ketoalkyl radical containing from about 8 to 20 carbon atoms, from 0 to 10 ethylene oxide moieties, and 0 or 1 glyceryl moiety; (b) polysorbates, such as sucrose esters of fatty acids, for example sucrose cocoate, sucrose behenate, and the like; (c) polyethylene oxide condensates of alkyl phenols, for example the condensation products of alkyl phenols having an alkyl group of 6 to 20 carbon atoms with ethylene oxide being present in amounts of about 10 to 60 moles of ethylene oxide per mole of alkyl phenol; (d) condensation products of ethylene oxide with the reaction product of propylene oxide and ethylene diamine; (e) condensation products of aliphatic alcohols having 8 to 18 carbon atoms with ethylene oxide, for example a coconut alcohol/ethylene oxide condensate having 10 to 30 moles of ethylene oxide per mole of coconut alcohol, the coconut alcohol fraction having 10 to 14 carbon atoms; (f) long chain tertiary amine oxides; (g) long chain tertiary phosphine oxides; (h) alkyl polysaccharides having a hydrophobic group of 6 to 30, preferably 10 carbon atoms and a polysaccharide group such as glucose, or galactose, suitable alkyl polysaccharides are octyl, nonydecyl, undecyldodecyl, tridecyl, tetradecyl, pentadecyl, hexadecyl, heptadecyl, and octadecyl, di-, tri-, tetra-, penta-, and hexaglucosides, galactosides, lactosides, glucoses, fructosides, fructoses, and the like; (i) polyethylene glycol (PEG) glyceryl fatty esters; (j) other nonionic surfactants that may be used include C-substituted 10-18 alkyl (C-substituted 1-6) polyhydroxy fatty acid amides such as C-substituted 12-18 methylglucamides, N-alkoxy polyhydroxy fatty acid amides, N-propyl through N-hexyl C-substituted 12-18 glucamides, and the like.

Amphoteric surfactants that may be used in the compositions of the invention are generally described as derivatives of aliphatic secondary or tertiary amines wherein one aliphatic radical is a straight or branched chain alkyl of 8 to 18 carbon atoms and the other aliphatic radical contains an anionic group such as carboxy, sulfonate, sulfate, phosphate, or phosphonate. Suitable amphoteric surfactants may be imidazolinium compounds, along with monocarboxylates or dicarboxylates such as cocamphocarboxypropionate, cocoamphocarboxypropionic acid, cocamphocarboxyglycinate, and cocoamphoacetate. Other types of amphoteric surfactants include aminoalkanoates or iminodialkanoates and mixtures thereof. Examples of such amphoteric surfactants include n-alkylaminopropionates and n-alkyliminodipropionates, which are sold under the trade name MIRATAINE by Miranol, Inc. or DERIPHAT by Henkel, for example N-lauryl-beta-amino propionic acid, N-lauryl-beta-imino-dipropionic acid, or mixtures thereof.

Zwitterionic surfactants are also suitable for use in the compositions of the invention. Zwitterionics include betaines, for example higher alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxylethyl betaine, and mixtures thereof. Also suitable are sulfo- and amido-betaines such as coco dimethyl sulfopropyl betaine, stearyl dimethyl sulfopropyl betaine, and the like. For MEs, the amount of surfactant may range from about 1 to about 40% by weight of the composition. For LCs, the amount of surfactant may range from about 5 to about 40% by weight of the composition.

Certain materials that have Hildebrand solubility parameters that are greater than 12 are relatively hydrophilic and are useful as co-solvents, which help in partitioning the peroxide at the oil-water interface and will more readily form part of the water phase of the aqueous oxidizing agent composition. Accordingly, the compositions of the present invention also include a water-soluble co-solvent having a Hildebrand solubility parameter value above 12.00 $(cal/cm^3)^{1/2}$. The amount of the co-solvent may range from about 1% to about 40% by weight of the composition. Suitable co-surfactants include, but are not limited to, monohydric or polyhydric alcohols, polyols, and the like. Suitable monohydric alcohols include, without limitation, ethanol and propanol. Suitable polyhydric alcohols include, without limitation, glycerine and glycols, include propylene glycol, butylene glycol and ethylene glycol. Suitable polyols include polyethylene glycols. Suitable sugars include glucose, fructose, mannose, mannitol, malitol, lactitol, inositol, and the like.

The stability of the compositions of the present invention may be further enhanced by use of chelating agents, such as ethylenediaminetetraacetic acid (and their salts) and phosphate buffers between the pH of 3.5 to 6.0.

While compositions of the present invention may be used in combination with conventional thickeners known for use in conventional whitening products, e.g. whitening strips, paint-on gels, trays, such thickeners are not required to provide whitening compositions of the present invention. Such thickeners include, without limitation, synthetic polymers, e.g. cellulose derivatives and carbomer polymers, natural and synthetic gums, and the like. In one embodiment the compositions are essentially free of such thickeners. By essentially free of, it is meant that the compositions do not contain such thickeners in amounts effective to appreciably increase viscosity compared to a composition that contains no such thickeners, for example less than about 0.4%, or less than about 0.1%, or even less than about 0.01%. In another embodiment the compositions are free of such thickeners.

The compositions may be used in any conventional whitening products for whitening teeth where they are compatible, including without limitation, whitening strips, paint-on compositions, toothpastes, trays, and the like. Such products may be used professionally by dentists in their office, or by individual consumers in their homes, depending on the nature of the products. Due to the fact that the ME or LC compositions of the present invention are substantially transparent or translucent, such compositions are particularly advantageous for use with flexible or permanently deformable whitening strips which themselves are socially non-obtrusive, i.e. substantially transparent.

The whitening product containing the composition of the present invention is applied to the teeth for a time effective to whiten the teeth. Depending on the particular whitening product and treatment regimen indicated for such product, the period of time may range from about 2 minutes to about 24 hours, or from about 2 minutes to about 1 hour, or from about 2 minutes to about 30 minutes, although longer or shorter periods of time may be used where appropriate or necessary. Whitening products containing compositions of the invention may be applied in a single application, or may be applied repeatedly at predetermined time intervals and under conditions known to those skilled in the art with respect to such known whitening products.

The following examples are provided to exemplify certain embodiments of the current invention, although they are not intended to limit the scope of the invention of claims appended hereto.

EXAMPLES

Liquid crystal whitening formulations were prepared according to Table 1 and Table 2. The sample of Table 1 had a pH of 4.8 (Sample 1). Sample 1 was split into two equal parts. The pH of the second part was adjusted to 5.5 using NaOH (Sample 2). The sample of Table 2 (pH 3.2, Sample 3) was split into thirds. One third was pH adjusted to 4.5 (Sample 4). The other third was pH adjusted to 5.8 (Sample 5). Two comparative samples were prepared by combining hydrogen peroxide with Carbopol 980 (Sample 6) for one comparative and Carbopol 956 (Sample 7) for the other. The hydrogen peroxide concentration was 6 percent by weight of the composition for each. The peroxide release, whitening efficacy, chemical stability and physical stability of some of these samples were evaluated. The data is shown in Tables 3, 4, and 5.

TABLE 1

| Trade Name | INCI name | w/w % |
| --- | --- | --- |
| Deionized water | Water | 7.9 |
| Tween-80 | Polysorbate-80 | 30.0 |
| Crodamol IPM | Isopropyl myristate | 25.0 |
| Emery 917 | Glycerin | 20.0 |
| Hydrogen Peroxide, 35% | Hydrogen peroxide | 17.1 |
| | Total | 100.0 |

TABLE 2

| Ingredients | w/w (%) | Solubility Parameter $(cal/cm^3)^{1/2}$ |
| --- | --- | --- |
| Water | QS | |
| Hydrogen Peroxide (35%) | 18.00 | |
| Tween 80 | 30.00 | |
| Isopropyl Myristate | 30.00 | 8.02 |
| Glycerine | 20.00 | 16.26 |
| Potassium Phosphate | 0.05 | |
| Disodium EDTA | 0.02 | |
| Phosphoric Acid | to pH 3.5-6 | |
| Total | 100.00 | |

Peroxide Release Properties:

The peroxide release from LQ whitening gels was measured using an established peroxide release model. The gel was placed on bovine teeth. The teeth were placed in a beaker with synthetic saliva up to the height of the teeth. The beakers were placed on a shaker and lightly shaken. The synthetic saliva was sampled at various times and analyzed for hydrogen peroxide content. Table 3 shows the percentage of peroxide released from the gels as a function of time.

TABLE 3

| Time (min) | 0 | 3 | 6 | 9 | 15 | 20 | 30 | 40 |
|---|---|---|---|---|---|---|---|---|
| Sample 6 | 0.0 | 2.8 | 4.5 | 5.2 | 3.1 | 1.9 | 0.5 | 0.2 |
| Sample 2 | 0.0 | 0.8 | 1.5 | 3.3 | 4.0 | 4.8 | 5.7 | 5.9 |

The peroxide release results from the two gels suggests that the hydrogen peroxide is released more readily from Carbapol gels and hence may cause bleaching-related teeth sensitivity on repeated use, whereas the liquid crystal gel of the present invention releases peroxide gradually and is less likely to cause sensitivity.

Whitening Efficacy of Liquid Crystal Gels:

Whitening efficacy of a liquid crystal bleaching composition containing 6% hydrogen peroxide was compared to a Carbapol gel with the same peroxide load. The evaluation was carried out using an established in-vitro bleaching model and bovine teeth. The bovine teeth were randomized based on their pre-bleaching L and b values (key-whitening parameters based on CIE color space). All the teeth in each set (n=12) were subjected to ten treatments of 30 minute each, with 1 hour rest in saliva between each treatment. Table 4 shows the whitening results, as difference between pre and post bleaching L, a and b parameters.

TABLE 4

| Whitening efficacy | Sample 2 | | | Sample 6 | | |
|---|---|---|---|---|---|---|
| | L | a | b | L | a | b |
| Average | 12.35 | −0.898 | −6.5792 | 11.497 | −0.615 | −6.2525 |
| Std Dev | 4.3479 | 1.1228 | 3.5813 | 5.091 | 0.9454 | 2.3835 |

The whitening efficacy of the liquid crystal gel of the present invention was comparable to that of the Carbapol gel, despite having significantly different rheological properties.

The rheological properties of whitening gels are key determinants of their long term stability as well as the whitening efficacy. Whitening efficacy of these gels is directly proportional to their ability to release peroxide. The viscosity and hydrophobicity of the gels are key determinants of peroxide release function of the gels.

Rheological Properties:

Liquid crystal whitening gels possess significantly different rheology compared to the most commonly employed Carbapol and petrolatum gels. All comparative rheological studies were carried out at 25° C. From stain sweep measurements, it was determined that LQ whitening gels are viscoelastic, and the elasticity can be ranked slightly lower than Carbapol 980 and 956 gels. Moreover, LQ whitening gels have a unique complex viscosity that is significantly different than Carbapol and petrolatum gels.

A microemulsion whitening formulation was made according to Table 5 (Sample 8).

TABLE 5

| Ingredients | w/w (%) | Solubility parameter $(cal/cm^3)^{1/2}$ |
|---|---|---|
| Water | QS | |
| Hydrogen Peroxide (35%) | 18.00 | |
| PEG-6 Capric/Caprylic Glycerides | 25.00 | |
| Oleyl Alcohol | 8.00 | 8.95 |
| Glycerine | 12.00 | 16.26 |
| Mineral Oil | 7.00 | 7.09 |
| Clove Oil (Eugenol) | 3.00 | 11.12 |
| Potassium Phosphate | 0.05 | |
| Disodium EDTA | 0.02 | |
| Phosphoric Acid | to pH 3.5-6 | |
| Total | 100.00 | |

The chemical and physical stability of different liquid crystal and microemulsion whitening compositions were studied for 13 weeks at 40° C./75 RH, and compared to Carbapol gel containing the identical load of hydrogen peroxide.

Tables 6 and 7 below show the peroxide and pH properties (chemical and physical stability) of a typical 6% peroxide containing liquid crystal and Carbapol gel over time.

TABLE 6

| | Sample 2 | | Sample 6 | |
|---|---|---|---|---|
| Week | $H_2O_2$ @ 40° C. (%) | pH @ 40° C. | $H_2O_2$ @ 40° C. (%) | pH @ 40° C. |
| 0 | 6.12 | 4.85 | 6.01 | 4.79 |
| 1 | 5.92 | 4.30 | 5.70 | 4.50 |
| 2 | 6.04 | 4.01 | 5.42 | 3.90 |
| 3 | 6.04 | 4.00 | NA | 3.70 |
| 4 | 5.93 | 3.71 | 5.10 | 3.40 |
| 6 | 5.45 | 3.57 | 4.80 | 3.20 |
| 8 | 5.29 | 3.46 | 3.81 | 3.10 |
| 10 | 4.97 | 3.40 | 2.66 | 2.90 |
| 13 | 4.63 | 3.36 | 1.68 | 2.5. |

Sample 6 was runny after 8 weeks at 40° C., compared to Sample 2.

TABLE 7

| | Sample 8 | |
|---|---|---|
| Week | $H_2O_2$ @ 40° C. (%) | pH @ 40° C. |
| 1 | 6.1 | 4.67 |
| 2 | 6.0 | 4.70 |
| 3 | 5.8 | 4.20 |
| 5 | 5.9 | 4.20 |
| 6 | 5.7 | 4.12 |
| 8 | 5.6 | 4.16 |
| 10 | 5.5 | 4.13 |
| 13 | 5.4 | 4.10 |

The data above demonstrates the compositions of the present invention are chemically and physically stable, and are effective tooth whitening compositions.

We claim:
1. A method for whitening teeth comprising applying a composition to the teeth for a period of time and under conditions effective to whiten the teeth, the composition comprising,
   a whitening agent comprising a peroxide in an amount of from about 1% to about 35% by weight of the composition, a hydrophilic phase comprising water in an amount of from 1% to about 80% by weight of the composition, a hydrophobic phase comprising an oil in an amount of from 1% to less than 50% by of the composition, said oil being selected from the group consisting of olive oil, coconut oil, linseed oil, mineral oil, clove oil, isopropyl myristate and isopropyl palmitate, a surfactant selected from the group consisting of anionic, nonionic, amphoteric and zwitterionic surfactants; and a water-soluble co-solvent having a Hildebrand solubility parameter above 12 $(cal/cm^3)^{1/2}$, wherein the composition is in a form selected from the group consisting of a liquid crystal and a microemulsion, wherein the composition is free of a thickener selected from the group consisting of a synthetic polymer, a natural gum and a synthetic gum, and wherein and the hydrophilic phase is in predominant weight proportion relative to the hydrophobic phase in the composition.

2. The method according to claim 1 wherein the oil has a Hildebrand solubility parameter value ranging from about 5 to about 12 $(cal/cm^3)^{1/2}$.

3. The method according to claim 1 wherein the co-solvent is selected from the group consisting of monohydric alcohols, polyhydric alcohols, sugars and polyols.

4. The method according to claim 1 wherein the co-solvent is selected from the group consisting of ethanol, propanol, propylene glycol, butylene glycol, ethylene glycol, glycerine, glucose, fructose, mannose, mannitol, malitol, lactitol and inositol.

5. The method of claim 1 wherein the period of time ranges from about 2 minutes to about 24 hours.

6. The method of claim 5 comprising repeated application of the composition at predetermined time intervals.

7. The method of claim 1 wherein the weight ratio of the hydrophilic phase to the hydrophobic phase ranges from about 1.5:1 to about 10:1.

8. The method of claim 2 wherein the weight ratio of the hydrophilic phase to the hydrophobic phase ranges from about 1.5:1 to about 10:1.

\* \* \* \* \*